United States Patent [19]

Weiler et al.

[11] 4,305,923

[45] Dec. 15, 1981

[54] METHOD FOR QUANTITATIVE ANALYSIS FOR LIMONIN

[76] Inventors: Elmar W. Weiler, Brenscheder Str. 25, 463 Bochum, Fed. Rep. of Germany; Richard L. Mansell, 13508 Little Lake Pl., Tampa, Fla. 33612

[21] Appl. No.: 147,732

[22] Filed: May 8, 1980

[51] Int. Cl.³ ............... G01N 33/54; A61K 43/00
[52] U.S. Cl. ........................... 424/1; 435/7; 435/28; 23/230 B; 424/12
[58] Field of Search ............ 435/7, 28, 188; 23/230 B; 424/1, 8, 12

[56] References Cited

U.S. PATENT DOCUMENTS

| | | | |
|---|---|---|---|
| 3,911,103 | 10/1975 | Hasegawa et al. | 426/51 |
| 3,920,851 | 11/1975 | Hasegawa et al. | 426/51 |
| 3,959,650 | 5/1976 | Lukens, Jr. | 424/1 |
| 3,989,854 | 11/1976 | Chandler et al. | 426/398 |
| 4,145,407 | 3/1979 | Parsons, Jr. et al. | 424/1 |

OTHER PUBLICATIONS

Weiler E. W. et al., "Radioimmunoassay of Limonin Using a Tritiated Tracer", Jour. Agric. Food & Chemistry, vol. 28, pp. 543-545 (May-Jun. 1980).
Weiler E. W. et al., "Radioimmunoassay for the Determination of Limonin in Citrus", Phytochemistry, vol. 19, pp. 1403-1407 (1980).
Nicol K. J. et al., "The Extraction of the Enzyme Degrading the Limonin Precursor in Citrus Albedo", J. Sci. Food Agric., vol. 29, pp. 795-802 (1978).

*Primary Examiner*—Benoît Castel
*Attorney, Agent, or Firm*—Arthur G. Yeager

[57] ABSTRACT

Method for determining the amount of limonin in a sample by subjecting a mixture of the sample and a known amount of a labeled limonin derivative to reaction with limonin-specific antibodies, analyzing to determine the amount of reaction product of antibodies and labeled limonin derivative, and applying the result to a previously prepared correlation to determine the amount of limonin in that sample.

7 Claims, No Drawings

METHOD FOR QUANTITATIVE ANALYSIS FOR LIMONIN

BACKGROUND OF THE INVENTION

This invention relates to a rapid, sensitive and specific assay for limonin, allowing the detection and quantification of this most important bitter constituent of citrus juice, e.g. grapefruit juice.

The determination of limonin on a routine basis today is extremely difficult. This compound occurs in very low levels in plant material, and only 5 parts per million of it give grapefruit juice an unacceptably bitter taste. The present conventional analytical methods (thin layer chromatography, high performance liquid chromatography) are very difficult and very slow in determining these low levels of limonin within the high concentrations of contaminants. Normally this requires the preparation of purified and concentrated extracts for analysis. The time required for analysis is one day or even more, which is prohibitive in a quality control procedure.

It is an object of this invention to provide a procedure for a rapid and precise analysis of limonin in unpurified plant extracts (e.g. grapefruit juice) even at exceedingly low levels (down to 1–10 parts per billion). The assay time is short, normally less than one hour.

BRIEF DESCRIPTION OF THE INVENTION

This invention provides a method for quantitative analysis of a sample for its content of limonin by preparing a mixture of a sample containing an unknown quantity of limonin and a known amount of a readily detectible limonin derivative, reacting said mixture with a known amount of limonin-specific antibodies, analyzing the reaction product for the amount of said limonin derivative that has reacted with said antibodies, comparing the analysis results with a predetermined standard correlation of the amount of said limonin derivative known to react with said antibodies in the presence of varying amounts limonin. In specific embodiments of this invention the limonin derivative is limonin-7-(O-carboxymethyl) oxime reacted with peroxidase enzyme or reacted with tyrosine methyl ester iodinated with iodine-125 isotope.

DETAILED DESCRIPTION OF THE INVENTION

The procedure of this invention involves the use of various limonin derivatives which are believed to be novel. Limonin itself has the following configuration

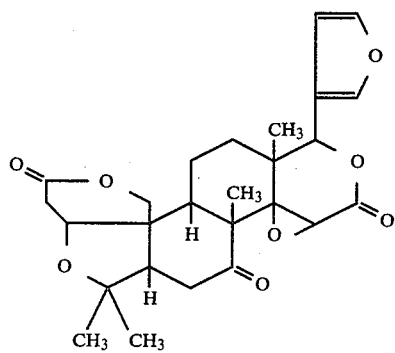

One of the limonin derivatives preferred in this invention is limonin-7-(O-carboxymethyl) oxime which is the above structure with the carbonyl oxygen in the 7-position replaced by $=N-O-CH_2-COOH$. This derivative provides a bridge to which other component groups can be attached while leaving the functionality of the original limonin substantially unchanged. Within the context of this invention three of such component groups are particularly important; namely (1) a protein, (2) an enzyme, and (3) a compound containing a radioactive isotope.

The first of these reaction products is a limonin-protein conjugate that can be injected into an animal to cause the production of antibodies that are specifically reactive to limonin. It has been found that if limonin-7-(O-carboxymethyl) oxime is reacted with bovine serum albumin, the resultant conjugate when injected into an animal produces antibodies with a high degree of selectivity for limonin. Such antibodies are employed in the process of this invention. Other types of protein may be used for this purpose, although bovine serum albumin is preferred.

The other two component groups that may be employed with limonin-7-(O-carboxy-methyl) oxime, i.e. an enzyme and a compound with a radioactive isotope, are for the purpose of producing a tracer that is readily and rapidly detectible by known analytical techniques. With respect to the enzyme-limonin adduct it has been found preferable to employ peroxidase as the enzyme, most preferably, horseradish peroxidase. With respect to the radioactive isotope-limonin compound, a preferred component is tyrosine methyl ester iodinated with iodine-125.

The process of this invention begins with the preparation of the limonin derivatives that are to be used in the analysis. Limonin-7-(O-carboxymethyl) oxime can be prepared by reacting limonin with aminooxyacetic acid under suitable conditions as described hereinafter. The oxime is coupled to bovine serum albumin in a cold alkaline solution and the resulting limonin-protein conjugate is employed to innoculate rabbits. Antibodies developed in the rabbits are removed and isolated in the form of purified gammaglobulin fractions containing these antibodies which are specifically reactive with limonin. A known amount of antibodies is contacted with a mixture of a sample volume containing an unknown amount of limonin and a volume of tracer containing a known amount of limonin-derivative tracer (either enzyme-limonin or radioactive limonin). There are competing reactions in which the limonin in the sample and the limonin-derivative tracer are competing with each other to react with the antibodies. After a given contact time the reaction medium is analyzed for the quantity of limonin-derivative tracer that has reacted with antibodies. This information is then employed to calculate the unknown amount of limonin in the sample. A simple calculation means is the use of a graph showing a correlation based on experimental data obtained from analyses of several reaction mixtures resulting from a given amount of tracer and several known amounts of limonin reacting with a given amount of antibodies.

The reagents and derivatives of this invention are especially designed for use in immunological assays. However, the actual assay performance, whether it be liquid phase or solid phase, is not critical. Assay conditions have been optimized and selected ensuring maximum reproducibility, maximum speed and ease of use for routine purposes. These include the performance of the solid-phase technique used for enzyme immunoassay. Among the advantages of this invention are:

1. Immunological assay of limonin is more sensitive than prior methods by a factor of 1000–10,000. Consequently, levels of this bitter compound may be detected in the 1 part per billion range without need for extract concentration.

2. Immunological assay of limonin is more specific and reproducible than prior methods. Limonin may be detected and quantitated in unpurified extracts.

3. Immunological assay is much more rapid than other methods. Overall assay times can be shortened to less than 1 hr. Consequently, these procedures are useful as quality control procedures. Provided the assay is supplied as an optimized kit, it involves only very few steps which are simple to perform, especially in solid-phase enzyme immunoassay.

4. Automated performance of the assays is possible. This ensures capacities of many hundred to thousands of analyses per day, which is more, by a factor of at least 100, than can be performed with conventional techniques. This makes immunoassay of limonin applicable to many analytical problems connected with the breeding and/or selection of low limonin or even limonin-free citrus varieties.

There are several potential uses for the process of this invention other than those mentioned above. It provides a highly efficient screening method for selecting limonin-low or limonin-free varieties of citrus in breeding or cell culture programs. More than 2000 limonin analyses may be performed by one worker within a single working day. This is, by a factor of 100–1,000, more than can be done with conventional assay methods. As a consequence, only immunoassays, especially the mechanized radioactive assay, will be useful in these screening studies. Thus, this assay is a prerequisite for the future build-up of new citrus varieties with controlled low content of limonin. The industrial potential of these strains which can only be found with immunoassay screening, speaks for itself. The sensitivity of immunoassay makes it useful in application to the selection of limonin-free cell lines of citrus in cell culture. Selection of mutant cell lines which are incapable of further limonin production thus becomes possible. Plants can be regenerated from these mutant lines. The selection must be sensitive because analyses must be performed on a few cells in culture. Only the immunological assay provides such sensitivity. Investigations can also be made on metabolism of limonin (biosynthesis and degradation), its distribution and regulation of its levels in all parts of the plant. These investigations can include the possibility of regulating limonin biosynthesis with chemical or hormonal agents.

The invention will be further clarified with reference to the following illustrative embodiments, which are intended to be exemplary only, and not to limit the scope of the invention. Parts and percentages are by weight unless otherwise specified.

EXAMPLE 1

Preparation of limonin-7-(O-Carboxymethyl) oxime.

Functionalization of limonin at a specific site to yield a stable reactive product to be used in the synthesis of other immunochemicals.

Procedure: A typical procedure is given: 300 mg limonin and 600 mg aminooxyacetic acid were refluxed for 2 hrs in 24 ml pyridine-95% ethanol (1:1). The solvents were evaporated under vacuum and yielded an oily residue. The residue was extracted with 100 ml of acetonitrile and the supernatant was chromatographed on thin layer chromatograph plates (silica gel, 0.5 mm thickness) in the solvent system benzene, 95% ethanol, glacial acetic acid, water (200:47:1:15). The band at $R_f=0.19$ was eluted with acetonitrile and upon concentration, 200 mg of crystalline material was obtained. Needles, mp 256° C. (decomp.).

Limonin-7-(O-carboxymethyl) oxime; in dichloromethane was treated with etheral diazomethane to give the methyl ester (R=0.47 in the above thin layer system limonin $R_f=0.37$). Needles, mp 124°–127° C. IR. delta lactone 1735; C=N 1626 (Limonin lactone 1750,C=O 1706). MS:M+ m/e558 (calculated for $C_{29}H_{35}O_{10}N$: 557.6) Elemental analysis of limonin-7-(O-carboxymethyl) oxime (Found: C,56.17;H,6,36; N,2.37, $C_{28}H_{33}O_{10}N.3H_2O$ requires: C,56.27; H,6.58, N2.34%).

EXAMPLE 2

Coupling of limonin-7-(O-carboxymethyl) oxime to bovine serum albumin 33.3 micromol (18.1 mg) (limonin 7-(O carboxymethyl) oxime were dissolved in 2 ml of dimethylformamide and 54 micromol (10 micro l.) tri-n-butylamine added. The solution was cooled to 0° C. and 36.5 mol (5 micro l.) isobutylchlorocarbonate was added. After stirring for 20 minutes, the mixture was added to an ice cold solution of 420 mg bovine serum albumin in 7 ml dimethylformamide/water (1:1) containing 0.14 ml of 1 N sodium hydroxide. 0.3 ml of dimethylformamide was added to clear the solution and the reaction mixture was stirred for 60 minutes. 0.07 ml of 1 N sodium hydroxide was added and stirring was continued for 3 hours. Finally, the conjugate was dialyzed against 2 liters of 10% dimethylformamide overnight, against distilled water for 3 days and was then lyophilized. Coupling ratios were determined from spectral data (490 nm) in concentrated sulfuric acid and the limonin/protein ratio was found to be 16:1.

EXAMPLE 3

Preparation of $^{125}$I-Tyrosinemethylester-limonin

A typical method for the preparation of the tyrosine methylester and the radioiodinated derivative is given: 37 micromol (20.1 mg) of limonin-7-(O-carboxymethyl) oxime were dissolved in 1 ml of dimethylformamide and chilled to 0° C. 52 micro 1 of 10% triethylamine in dimethylformamide (v/v) were added and the reaction mixture cooled to −10° C.50 micro 1 of 10% isobutylchlorocarbonate in dimethylformamide (v/v) were added and after 3 minutes, 37 micro 1 mol (8.6 mg) tyrosine methylester and 0.1 ml 10% triethylamine in dimethylformamide were added and the reaction mixture stirred for 3 hours.

The limonin-7-(O-carboxymethyl)oxime-tyrosine methylester ($R_f=0.13$ in chloroformethylacetate (1.1)) gave a positive reaction with diazotized sulfanilic acid for tyrosine and the characteristic sulfuric acid color for limonoids. It was purified by thin layer chromatography and was obtained chromatographically pure. Limonin-7-(O-carboxymethyl) oxime-tyrosine methylester (TME-limonin) was iodinated to specific activities of at least 600–800 (Ci/mmol (calculated) by the chloramine T method of W. Hunter and R. C. Greenwood in Nature, volume 194, page 495 in 1962. The $^{125}$I-TME-limonin was purified by thin layer chromatography ($R_f=0.23$ in benzene ethanol-acetic acid-water. (200:47:1:15)) and eluted and stored in methanol.

EXAMPLE 4

Preparation of enzyme-labelled limonin tracer Limonin-O-carboxymethyl-oxime is bound to Horseradish Peroxidase via a mixed anhydride reaction to yield a highly substituted, stable enzyme-labeled limonin tracer which is reactive in immunoassay.

A typical procedure is given:

4.6 mg pure limonin-O-carboxymethyl-oxime is dissolved in 0.1 ml dry dimethyl formamide. 3–4 micro l. of tri-n-butylamine is added, and the mixture is cooled to $-15°$ C. Then 3–4 micro l. isobutylchlorocarbonate is added and the reaction allowed to complete for 20 minutes. The reaction mixture is then added to a solution of 5.3 mg horseradish peroxidase (Sigma Type III or similar material) in 0.18 ml of 0.5% $NaHCO_3$ and 0.18ml dioxane, cooled to $0°$ C. The activated limonin derivative is added in portions of 10 micro l. at 10 minute intervals, the reaction mixture is kept cool during the whole time. After the last addition, the reaction is allowed to complete for a further 45 minutes, then 1.8 ml of phosphate buffer is added (pH 7.0). The mixture is then purified by dialysis against phosphate buffer pH 7 preferably at $4°$ C.

The purified material may be used as it is and the stock solution diluted for immunoassay. For prolonged storage, the material may by lyophilized and the dry product stored refrigerated. Prior to use it is reconstituted with distilled water.

EXAMPLE 5

Performance of solid-phase coated-tube enzyme immunoassay

The material synthesized by the procedure of Example 4 is, in general, usable for any enzyme immunoassay performance known. However, the recommended procedure is the following: Purified gammaglobulin fractions containing specific limonin antibodies are used to coat the walls of polystyrene reagent tubes or similar surfaces with limonin specific antibodies. These tubes are used for incubation with an unknown amount of limonin (as contained in the sample) and a constant amount of enzyme-labeled tracer limonin. The distribution of enzyme activity bound to the walls and present in solution is correlated with the amount of limonin present in the sample. By determination of the enzyme activity bound to the walls of the tubes it is thus possible to calculate the unknown limonin concentration. After decanting and washing the incubated tubes, they are filled with the substrate solution for enzyme activity assay. After a certain period of time, the optical density of the solution is read in a spectrophotometer or colorimeter. Results are calculated from known limonin amounts included in the assay.

Procedures:

a. Preparation of gammaglobulins from total serum. This is performed by ammonium sulfate fratenation according to literature procedures.

b. Coating of polystyrene tubes with limonin-antibodies. The fraction of serum prepared according to (a) is stored lyophilized. Prior to use, it is dissolved in 50 mm $NaHCO_3$, pH 9.3 to a concentration of 1 mg/ml.

Tubes are coated with a constant volume of this solution for 3–24 hours (time is not critical but must be kept constant throughout) After coating, tubes are washed once with 0.01% bovine serum albumin in phosphate buffered saline pH 7.4 for 1 hr. This time is not critical but must be kept constant throughout. It is recommended to incubate at $4°$ C. Volume of washing soln. is 1.5 times volume used for coating. Tubes may be stored dry over silica gel at $4°$ C. for several weeks.

c. Enzyme immunoassay.

1. Incubation.

An aliquot of properly diluted plant extract (e.g. fruit juice) is incubated with a selected amount of dilute horseradish peroxidase labeled limonin in a PBS buffer pH 7.4. Incubation time is not critical but must be kept constant throughout, especially when using short incubation periods (less than 2 hrs.). Incubation times may be as short as 15–20 min, and as long as 24 hrs. It is recommended to perform long term incubations at $4°$ C. After incubation, tubes are decanted and washed 2 times with 1.5 times the incubation volume (which normally is 0.9 ml) of cold PBS.

2. Enzyme activity assay. (modified literature procedure) The assay solution contains: 0.1 m Sodium phosphate buffer pH 7.25 containing 2 mm 2-Aminoantipyrine, 25 mm. phenol, and per 22 ml of this solution 20 micro l. of 3% $H_2O_2$ which is added prior to use. 2 ml of this solution is incubated with the tubes. Incubation times and temperatures are not critical, but must be kept constant throughout, e.g., incubation may be performed for 5 min at $37°$ C. or for 10 min at room temperature. Optical densities are then read at 492 nm using colorimeters or spectrophotometers, and amount of limonin present may be calculated by extrapolating from a calibrated standard curve.

Typical assay protocol:

(assay samples and calibrators in duplicate) Add 0.6 ml of buffer, containing the limonin tracer and 0.1 ml of dilute sample (or calibrator) to precoated tubes and incubate (after mixing).

Decant and wash once with 1.5 ml of PBS.

Decant and add 2 ml of enzyme assay solution. Incubate 10 min at room temperature.

Read O.D. at 492 nm. Plot O.D. for the known concentrations on lin/log paper. Read concentrations of unknown samples from this standard curve.

Sensitivity of assay: Measuring range is from 0.5 ng. to 100 ng per sample, i.e. from 6 ppb to 1 ppm.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A method for quantitative analysis of limonin which comprises reacting a known amount of limonin-specific antibodies, with a mixture of a known volume of sample containing an unknown amount of limonin and a known amount of a limonin-derivative labeled with an enzyme or with a radioactive isotope, determining the amount of labeled limonin-derivative which has reacted with said antibodies and calculating therefrom the unknown amount of limonin in said sample.

2. The method of claim 1 wherein said limonin-derivative is limonin-7-(O-carboxymethyl) oxime.

3. The method of claim 1 wherein said limonin-derivative is enzyme labeled and is the reaction product of limonin-7-(O-carboxymethyl) oxime and horseradish peroxidase.

4. The method of claim 1 wherein said limonin-derivative is labeled with radioactive isotope and is the reaction product of limonin-7-(O-carboxymethyl) oxime and tyrosine methylester.

5. The method of claim 1 wherein said limonin-specific antibodies are produced by immunization of an animal with a limonin-7-(O-carboxymethyl)oxime conjugate.

6. The method of claim 5 wherein said protein is bovine serum albumin.

7. The method of claim 1 wherein said antibodies are coated on the inside surface of a tube and the limonin-derivative is labeled with an enzyme.

* * * * *